(12) United States Patent
Fidler (10) Patent No.: US 11,221,380 B2
(45) Date of Patent: Jan. 11, 2022

(54) METHOD AND APPARATUS FOR ANALYZING A SAMPLE VOLUME COMPRISING MAGNETIC PARTICLES

(71) Applicant: FRAUNHOFER-GESELLSCHAFT ZUR FOERDERUNG DER ANGEWANDTEN FORSCHUNG E. V., Munich (DE)

(72) Inventor: Florian Fidler, Wuerzburg (DE)

(*) Notice: Subject to any disclaimer, the term of this patent is extended or adjusted under 35 U.S.C. 154(b) by 441 days.

(21) Appl. No.: 15/054,224

(22) Filed: Feb. 26, 2016

(65) Prior Publication Data

US 2016/0178710 A1 Jun. 23, 2016

Related U.S. Application Data

(63) Continuation of application No. PCT/EP2014/068303, filed on Aug. 28, 2014.

(30) Foreign Application Priority Data

Aug. 30, 2013 (DE) .................. 10 2013 109 467

(51) Int. Cl.
  *G01R 33/12* (2006.01)
  *G01N 27/74* (2006.01)
  *G01N 15/06* (2006.01)

(52) U.S. Cl.
  CPC ....... *G01R 33/1223* (2013.01); *G01N 27/745* (2013.01); *G01R 33/1276* (2013.01); *G01N 15/0656* (2013.01)

(58) Field of Classification Search
  None
  See application file for complete search history.

(56) References Cited

U.S. PATENT DOCUMENTS

| 5,001,424 A | 3/1991 | Kellett et al. |
| 6,110,660 A | 8/2000 | Kriz et al. |
| 2009/0243603 A1* | 10/2009 | Makiranta ............... B03C 1/015 324/225 |

(Continued)

FOREIGN PATENT DOCUMENTS

| DE | 19946656 A1 | 8/2000 |
| EP | 1262766 A2 | 12/2002 |
| JP | 200690825 A | 4/2006 |

(Continued)

OTHER PUBLICATIONS

International Search Report and Written Opinion received for International Patent Application No. PCT/EP2014/068303, dated Nov. 5, 2014, 20 pages including 9 pages of English translation.

(Continued)

*Primary Examiner* — Jermele M Hollington
*Assistant Examiner* — Suresh K Rajaputra
(74) *Attorney, Agent, or Firm* — Dorsey & Whitney LLP (57) ABSTRACT

The described embodiments relate to a method for analyzing a sample volume including magnetic particles. The method may include applying an electric excitation signal to a measuring coil so as to generate a magnetic field acting on the sample volume using the measuring coil. Furthermore, the method may include sensing an electric measurement signal dependent on the inductance of the measuring coil and analyzing magnetic permeability of the sample volume using the measurement signal.

12 Claims, 5 Drawing Sheets

(56) References Cited

U.S. PATENT DOCUMENTS

2012/0164916 A1    6/2012  Kordonski et al.

FOREIGN PATENT DOCUMENTS

| | | |
|---|---|---|
| JP | 200956232 | 3/2009 |
| JP | 2009534641 A | 9/2009 |
| JP | 2011163832 A | 8/2011 |
| JP | 201311444 A | 1/2013 |
| WO | 2007122293 | 11/2007 |
| WO | 2008145813 | 12/2008 |
| WO | 2015028569 | 3/2015 |

OTHER PUBLICATIONS

Gleich, et al., Gleich, et al. "Tomographic imaging using the nonlinear response of magnetic particles" Nature (Journal), vol. 435, No. 7046, Jun. 30, 2005, Nature Publishing Group, UK.

\* cited by examiner

METHOD AND APPARATUS FOR ANALYZING A SAMPLE VOLUME COMPRISING MAGNETIC PARTICLES

RELATED APPLICATIONS

This Application is a continuation of International Application PCT/EP2014/068303, with an international filing date of Aug. 28, 2014. The International Application PCT/EP2014/068303 claimed priority to German Patent Application 10 2013 109 467.8 filed on Aug. 30, 2013. The entire contents of the foregoing prior filed applications are hereby incorporated herein by reference.

BACKGROUND

In technology and medicine, there is a wide field of application for nanoparticles having magnetic properties. They may be used as markers for specific properties, such as the vitality of cells, as contrast agents or as tracers for illustrating flow or vessels. The magnetic properties may be measured indirectly or directly.

One example for an indirect measurement method, for example, is magnetic resonance imaging (MRI), wherein substances containing iron or gadolinium are employed as contrast agents. Here, detection usually is by way of the changed relaxation properties of the surrounding protons. This allows for both determining the properties of the contrast agents and performing localization. There are a multitude of such particles and contrast agents having magnetic properties, including a number of functionalized particles. These are provided with special surface coatings and/or bonding sites in order to bond to special cells, for example. In the event of such bonds being effected, the particles both are located at the targets and may change their properties due to clustering, for example.

For the direct detection of magnetic particles, Gleich and Weizenecker, in Nature Vol 435/30 p. 1214ff, 2005, have presented a method for Magnetic Particle Imaging (MPI) capable of locating particles with a non-linear magnetization curve. This method is based on the fact that the magnetization of the particles has non-linearities only for small field strengths in an external alternating magnetic field, but reaches saturation for high field strengths, which then shows linear behavior. Across an additional field with a correspondingly great magnetic field formed so as to have a very small field or is field-free in a very small region, the field-free point (FFP), only the particles in this field-free point show non-linear magnetization behavior. Detection is done through measurement of the particles' magnetization. If higher harmonics of the frequency of the alternating field are found in the Fourier decomposition (spectrum), it can be gathered therefrom that particles are present in the field-free point, and an image can be calculated by scanning the sample with the field-free point. These higher harmonics are employed for evaluation.

SUMMARY

An implementation provides improved method and an improved apparatus for analyzing a sample volume comprising magnetic particles.

More particularly, one implementation provides a method and apparatus for analyzing a sample volume comprising magnetic particles in accordance with the main claims.

The approach described is suited as a detection method for magnetic particles. According to embodiments of the described approach, localization and additionally or alternatively measurement of the particle properties may be done by way of measuring the magnetic permeability. Advantageously, use of a single coil is sufficient here, which coil may be employed both to generate a magnetic excitation field acting on a sample volume and to obtain information on magnetic permeability of the sample volume. From the information on the magnetic permeability of the sample volume, for example, it can be gathered if at least one magnetic particle is present in the sample volume.

A method for analyzing a sample volume comprising magnetic particles comprises: applying an electric excitation signal to a measuring coil so as to generate a magnetic field acting on the sample volume using the measuring coil; sensing an electric measurement signal dependent on the inductance of the measuring coil; and analyzing magnetic permeability of the sample volume using the measurement signal.

Magnetic field lines of the magnetic field generated by the measuring coil may pass through the sample volume. The sample volume may be a region to be analyzed or a sample itself. For example, the sample volume may also include an area to be analyzed. According to different embodiments, the sample volume may be arranged inside the measuring coil, directly adjacent to the measuring coil or spaced from the measuring coil. Depending on the state of the sample volume, there may be no magnetic particles or at least one magnetic particle in the sample volume. A magnetic particle may be magnetic material, which may be introduced into the sample volume as a sample, for example. The measuring coil may comprise one coil winding or a plurality of coil windings. The coil may have a suitable shape, for example a cylindrical shape. The coil may be connected in a suitable circuit, for example a bridge circuit. The excitation signal may be applied to the measuring coil directly or via one or more elements. The excitation signal may be an alternating signal. Thus, the magnetic field may be an alternating field. For example, the excitation signal may be an alternating voltage or an alternating current. The measurement signal may represent an electric voltage. Such a measurement signal may be detected by way of voltage metering. For example, a voltage dropping over the coil may be sensed. The measurement signal may also represent an electric current. Such a measurement signal may be sensed by way of current measurement, for example by measuring the current flowing through the coil. The sensing the measurement signal and the applying the excitation signal may be executed simultaneously. The sensing and the applying may be executed over an extended period of time. If the excitation signal is an alternating signal, the measurement signal may be sensed while the excitation signal passes through one or more oscillation phases, for example. The inductance of the coil is dependent on the magnetic permeability of the sample volume. If the magnetic permeability of the sample volume changes, the inductance of the measuring coil changes. Thus, the measurement signal may indicate the magnetic permeability or a change in magnetic permeability of the sample volume. The analyzing the magnetic permeability of the sample volume may thus comprise evaluation of a quantity, a change and a temporal course of the measurement signal. Through evaluation of the measurement signal, information on the magnetic permeability of the sample volume may be obtained. Magnetic permeability of the sample volume may be the ratio of the magnetic flux density within the sample volume to the magnetic field strength within the sample volume. The information on the magnetic permeability may, in turn, be used to analyze a magnetic property of the matter within the sample volume, for example to detect at least one magnetic particle in the sample volume.

The acts of the method may be executed to measure the permeability of the sample volume. From the permeability curve of the sample volume resulting therefrom, the magnetization curve of the sample volume can be determined. In this way, both linear and non-linear magnetization curves can be determined.

The method may comprise comparing the measurement signal to a reference signal. The reference signal may be a reference voltage or a reference current, for example, as explained subsequently. Through the comparison, the magnetic permeability of the sample volume may be determined. The reference signal may represent a further electric measurement signal dependent on the inductance of the measuring coil while the measuring coil generates a magnetic field acting on a reference volume. The reference volume may comprise a reference sample, for example air. Thus, the measurement signal and the reference signal may be sensed at different times using the same measuring coil, once while the magnetic field acts on the sample volume (for determining the measurement signal) and once while the magnetic field acts on the reference volume (for determining the reference signal). At both times, the measuring coil may be excited by means of the same excitation signal. For example, the reference volume may be filled with a material of known magnetic properties, for example air. Thus, the sample volume may, for example, be a volume in which there is a sample, and the reference volume may be the same volume, but in which there is no sample. The reference signal may be sensed once and then stored. Thus, in the comparing, the measurement signal may be compared to a stored reference signal. The comparison may be performed by way of a suitable combination of the measurement signal and the reference signal. For example, the magnetic permeability may be determined on the basis of a difference between the measurement signal and the reference signal as well as a magnetic permeability associated with the reference signal. Thus, the magnetic permeability of the sample volume may be determined very easily.

According to one embodiment, a first contact of the measuring coil may be connected to a first terminal for applying the electric excitation signal via a first element, a second contact of the measuring coil may be connected to a second terminal for applying an electric balancing signal via a second element, and the second contact of the measuring coil may be connected to a measurement interface. The elements may, for example, be electric lines, resistors, capacitors or coils. An element may also represent a series connection and/or parallel connection of several elements. In the applying, the excitation signal may be applied to the first terminal and the balancing signal may be applied to the second terminal. In the sensing, the measurement signal may be sensed at the measurement interface. The balancing signal may represent a signal with which a reference voltage is present at the measurement interface if the magnetic field generated by the measuring coil acts on a reference volume. The reference voltage may have a certain voltage value, for example zero volts. A value or course of the balancing signal may have been determined during a reference measurement, wherein the magnetic field of the measuring coil acts on the aforementioned reference volume. This allows for using very simple circuits for providing the excitation signal and the balancing signal for analyzing the sample volume.

According to another embodiment, a first contact of the measuring coil may be connected to a first terminal for applying the electric excitation signal via a first element, a second contact of the measuring coil may be connected to a second terminal for applying an electric balancing signal via a second element, and the second contact of the measuring coil may be connected to a measurement interface. In the applying, the excitation signal may be applied to the first terminal and the balancing signal may be applied to the second terminal. In the sensing, the balancing signal may be sensed as the measurement signal. The balancing signal may be formed so as to set a certain reference voltage at the measurement interface depending on whether the magnetic field generated by the measuring coil acts on the sample volume or a reference volume. Thus, the balancing signal may be readjusted continuously so as to set the certain reference voltage. The reference voltage may be zero volts, for example. Advantageously, this way no reference measurement is necessary.

The method may comprise applying a further electric excitation signal to a further measuring coil so as to generate a further magnetic field acting on a further sample volume using the further measuring coil. Furthermore, the method may comprise sensing a further electric measurement signal dependent on the inductance of the further measuring coil. The further measurement signal may allow for analysis of the magnetic permeability of the further sample volume due to the dependence of the inductance of the further measuring coil on the magnetic permeability of the further sample volume. The two sample volumes may be identical, overlap each other at least partially or not overlap each other. In case the sample volumes overlap each other at least partially, a sample can be analyzed very accurately. For example, spatial distribution of the magnetic material within the sample can be analyzed.

The method may comprise determining a distribution of the magnetic particles in the sample volume and the further sample volume using the measurement signal, the further measurement signal and information on a position of the sample volume, a position of the further sample volume, information on a characteristic of the excitation signal and information on a characteristic of the further excitation signal. In this way, spatial distribution of the magnetic particles can be determined by way of suitable choice of the characteristics of the excitation signal is.

Additionally or alternatively, the method may comprise exposing the sample volume and the further sample volume to an additional magnetic field. Furthermore, the method may comprise determining a distribution of the magnetic particles in the sample volume and the further sample volume using the measurement signal, the further measurement signal and information on a characteristic of the additional magnetic field in the sample volume and the further sample volume. Thus, there is another way to determine the spatial distribution of the magnetic particles.

According to one embodiment, the method may comprise exposing the sample volume to an inhomogeneous additional magnetic field. In the analyzing, a distribution of the magnetic particles in the sample volume may be determined using the measurement signal and information on a spatial course of the additional magnetic field within the sample volume. The information on the spatial course may, for example, comprise information on a position of a portion of the additional magnetic field with low magnetic field strength.

The applying, sensing and the exposing may be executed multiple times, wherein the spatial course of the additional magnetic field may be changed in the repeated acts of exposing the sample volume. In the analyzing, the distribution of the magnetic particles may be determined using the measurement signal is sensed in the repeated acts of sensing and information on a change in the spatial course of the additional magnetic field during the repeated acts of exposing. Thus, for example, consecutive acts of sensing may be executed with a different spatial course of the additional magnetic field each. With the spatial course of the additional magnetic field during the sensing of the individual measurement signals being known, for example, a special distribution of the magnetic permeability or a spatial distribution of the magnetic particles within the sample volume can be determined.

An apparatus for analyzing a sample volume comprising magnetic particles comprises: a measuring coil formed to generate a magnetic field acting on the sample volume in response to application of an electric excitation signal to the measuring coil; and a measurement interface for sensing an electric measurement signal dependent on the inductance of the measuring coil, with the measurement signal allowing for analysis of the magnetic permeability of the sample volume due to the dependence of the inductance of the measuring coil on the magnetic permeability of the sample volume Such an apparatus is suitable for executing the acts of the aforementioned method for analyzing a sample volume comprising magnetic particles.

In such an apparatus, the sample volume may be arranged inside the measuring coil. In this way, for example, a sample arranged in a test tube may be analyzed. As an alternative, the sample volume may be arranged outside the measuring coil.

The apparatus may comprise a coil core guided through the measuring coil. One end of the coil core may be formed as a tip for exposing the sample volume. The magnetic field of the measuring coil may be concentrated on the sample volume through the tip. Moreover, the coil core may be used to bridge a spatial distance between the coil and the sample volume.

The apparatus may comprise evaluation means. The evaluation means may be formed to determine the magnetic permeability of the sample volume using the measurement signal. The magnetic permeability of magnetic particles allows for analyzing both the particles themselves and their environment.

According to one embodiment, a first contact of the measuring coil may be connected to a first terminal for applying the electric excitation signal via a first element, a second contact of the measuring coil may be connected to a second terminal for applying an electric balancing signal via a second element, and the second contact of the measuring coil may be connected to the measurement interface. In this way, the measuring coil may be included in a suitable bridge circuit.

The first element may be a capacitor or an electric line. The second element may be a resistor, a coil or an electric line. By way of a suitable choice of the elements, metrological properties of the apparatus can be adjusted.

The apparatus may comprise a further measuring coil. The further measuring coil may be formed to generate a further magnetic field acting on a further sample volume in response to applying a further electric excitation signal to the further measuring coil. The apparatus may further comprise a further measurement interface for sensing a further electric measurement signal dependent on the inductance of the further measuring coil. The further measurement signal may allow for analyzing the magnetic permeability of the further sample volume due to the dependence of the inductance of the further measuring coil on the magnetic permeability of the further sample volume. The sample volume is may be different or at least partially identical. The sample volume and the further sample volume may thus overlap at least partially. Using the further measuring coil, for example, a sample volume can be analyzed more accurately, or a larger sample volume can be analyzed, as compared with using only one measuring coil. The apparatus may comprise two, three or more measuring coils.

BRIEF DESCRIPTION OF THE DRAWINGS

Embodiments will be explained in greater detail in the following with reference to the appended drawings.

DETAILED DESCRIPTION

In the following description of embodiments, the same or similar reference numerals shall be used for similarly acting elements depicted in the various drawings, wherein repeated description of such elements shall be omitted.

Figure 1:
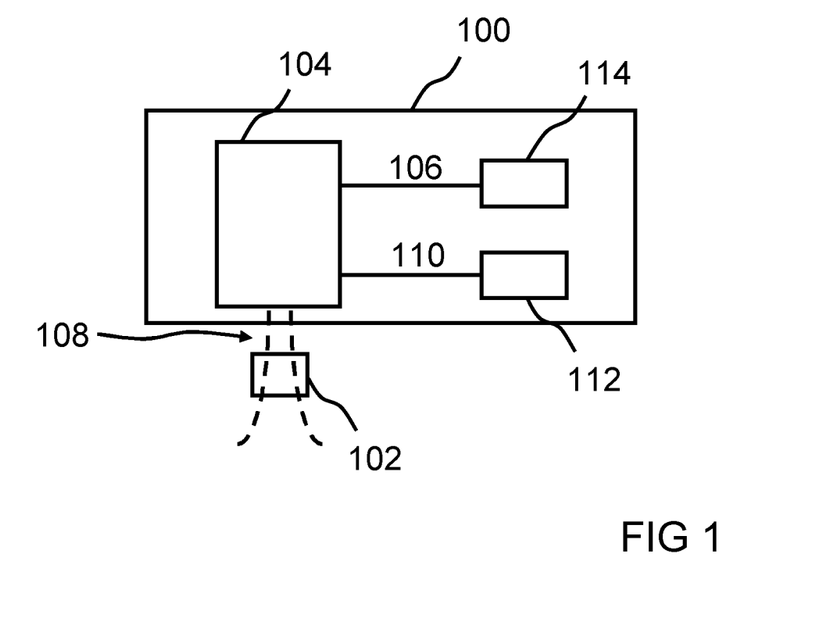
FIGS. 1 to 6 show schematic illustrations of an apparatus for analyzing a sample volume, according to embodiments.

FIG. 1 shows a schematic illustration of an apparatus 100 for analyzing a sample volume 102 comprising magnetic particles, according to an embodiment. The apparatus 100 comprises a measuring coil 104. The block 104 shown in FIG. 1 may represent the measuring coil or a circuit comprising the measuring coil, for example a bridge circuit. When an excitation signal 106, for example an electric voltage or an electric current, is applied to the measuring coil 104 via an interface during an analysis procedure, a magnetic field 180 is generated by the measuring coil 104.

The measuring coil 104 and the sample volume 102 are aligned with respect to each other so that the magnetic field 108 acts on the sample volume 102, for example pervades it. The sample volume 102 may also be regarded as a sample. The inductance of the measuring coil 104 is dependent on the magnetic permeability of the sample volume 102. Thus, the magnetic permeability of the sample volume 102 can be inferred from the inductance of the measuring coil 104. To this end, the measuring coil 104 is connected to a measurement interface for sensing a measurement signal 110 dependent on the inductance of the measuring coil 104. The inductance of the measuring coil 104 and thus the magnetic permeability of the sample volume 102 can be determined by way of the measurement signal 110.

According to this embodiment, the apparatus 100 comprises evaluation means 112 for evaluating the electric measurement signal 110. The evaluation means 112 is formed to receive the measurement signal 110 and to determine and provide an analysis result with respect to the sample volume 102 on the basis of the measurement signal 110. For example, the evaluation means 112 may be formed to determine a value of the magnetic permeability or a value dependent on the magnetic permeability of the sample volume 102. The measuring coil 104 and the evaluation means 112 may be arranged within a common housing. As an alternative, the measuring coil 104 and the evaluation means 112 may be arranged in separate housings. The apparatus 100 may comprise an interface for providing the measurement signal 110 to external evaluation means 112.

Thus, the apparatus 100 may be realized with or without evaluation means 112, according to different embodiments.

According to an embodiment, the evaluation means 112 is formed to conduct the analysis of the sample volume 102 using a reference signal. The reference signal may represent a stored measurement signal mapping the inductance of the measuring coil 104 during an analysis procedure during which the sample volume 102 corresponds to a reference volume.

According to an embodiment, the evaluation means 112 is formed to conduct the analysis of the sample volume 102 using a balancing signal. The balancing signal may correspond to a signal provided to the measuring coil or a circuit comprising the measuring coil during the analysis procedure.

According to this embodiment, the apparatus 100 comprises excitation means 114 for providing the excitation signal 106. The excitation means 114 may, for example, be formed as a current source or a voltage source. The measuring coil 104 and the excitation means 114 may be arranged within a common housing. As an alternative, the measuring coil 104 and the excitation means 114 may be arranged in separate housings. The apparatus 100 may comprise an interface for receiving the excitation signal 106 from the excitation means 114. Thus, the apparatus 100 may be realized with or without the excitation means 114, according to different embodiments.

The apparatus 100 may comprise the sample volume 102, for example a receptacle, such as a container, for a sample, or the sample volume 102 may be arranged adjacent to the apparatus 100.

According to the embodiment shown in FIG. 1, the sample volume 102 is or may be arranged adjacent to the measuring coil 104, outside the apparatus 100. For example, the sample volume 102 may be arranged along a longitudinal axis of the measuring coil, which is formed as a cylindrical coil, for example.

For the analysis of the sample volume 102, the sample volume 102 may be moved toward the apparatus, or vice versa.

According to an embodiment, the analysis procedure is based on measuring the magnetic permeability of the sample 102 or sample volume 102. The parameter in form of the magnetic permeability is advantageous because it allows for particularly suitable construction of the measuring apparatus 100.

According to an embodiment, the magnetic permeability of the sample 102 is measured by measuring the inductance of the measuring coil 104. To this end, an alternating magnetic field 108 of a certain strength is generated by the measuring coil 104 and either current or voltage is measured at this coil 104. Therefrom, the magnetic permeability of the sample 102 can be determined at the field strengths cycled through by the alternating field 108.

Local association of the determined magnetic permeability can be done by locally varying, e.g. by varying a gradient, either the strength of the phase of this alternating field 108. This variation may, for example, be a wave running through spatially, where the phase of a sinusoidal excitation changes over space.

By additionally applying, e.g. by separate means, as subsequently shown with respect to FIG. 5, for example, a locally different static or quasi-static magnetic field, local association can be done by variation thereof. When measuring the inductance, the derivative of the magnetic permeability may be measured. According to an embodiment, for local association, it is necessary for the magnetic permeability to be dependent on the field strength.

According to an embodiment, the sample volume may be exposed to an additional inhomogeneous magnetic field. This may be employed for an imaging method. According to an embodiment, the additional magnetic field is realized such that it has a very small field within the sample volume or has a field-free point and is large in all other points of the sample volume, for example so large that it causes saturation of particles arranged there. The magnetic flux of particles saturated by the large additional magnetic field does not change significantly with field variations through the measuring coil 104. Hence, the measurement signal 110 may be associated with the region of the sample volume 102 in which the additional magnetic field has the low field strength. According to an embodiment, using the measuring coil 104, the permeability of the sample volume 102 is measured continuously, i.e. measurement signals 110 are sensed, while the field-free point of the additional magnetic field is moved mechanically or electrically. In this manner, an image may be rasterized.

According to an embodiment, the spatial distribution of magnetic particles in the sample volume 102 may thus be ascertained. Generally speaking, to this end there may be employed an additional magnetic field whose the spatial course of its magnetic field strength has a first portion of low magnetic field strength and a second portion of higher magnetic field strength as compared with the first portion. During an analysis time period, the spatial location of the two portions within the sample volume 102 is changed. This leads to a spatial change of the magnetic permeability of the particles within the sample volume 102. A plurality of measurement signals 110, which depend on the change of the spatial location of the portions of the additional magnetic field, are sensed during the analysis time period. Information on the spatial distribution of the magnetic particles within the sample volume 102 may be ascertained by evaluating the plurality of measurement signals 110. The information on the spatial distribution may, for example, be used by an imaging method so as to ascertain an image representation of the spatial distribution of the particles within the sample volume 102.

The information on the spatial distribution may, for example, be determined by the evaluation means 112. To this end, the evaluation means 112 may be formed to combine information on the change of the additional magnetic field, for example information on a temporal and spatial course of the location of the first portion, for example of a field-free point of the additional magnetic field, with the plurality of measurement signals 110. For example, each of the plurality of measurement signals 110 may be associated with the current location of the first portion of the additional magnetic field at the time of sensing a measurement signal 110. Thus, each of the measurement signal's 110 may be associated with a position within the sample volume 102.

Figure 5:
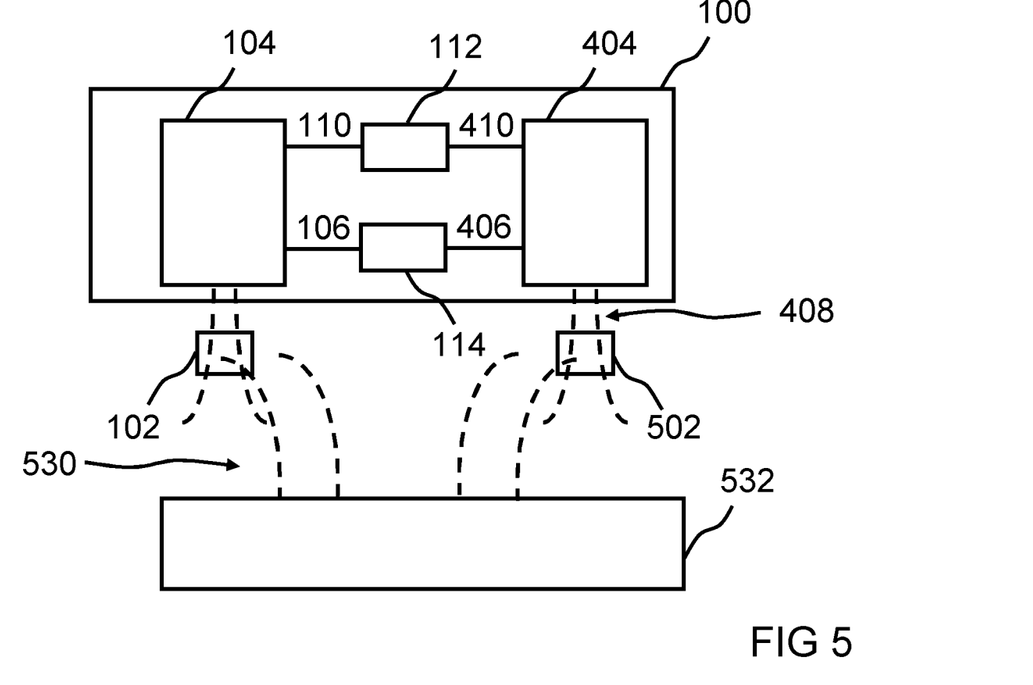

The additional magnetic field may, for example, be generated by means for generating the additional magnetic field, as shown in FIG. 5.

According to an embodiment, local measurement with a locally sensitive coil 104 may also be employed for detecting particles.

The magnetic permeability differs from the magnetization as used in Magnetic Particle Imaging (MPI). Therein, it usually is excluded to use the information on the excitation frequency. Furthermore, no signal is used therein at high field strengths because the particles are in saturation and thus the magnetization does not change.

If a described installation is brought into a very strong field, such as a magnetic resonance tomograph, particles have a magnetic permeability which can be measured, but the magnetization does not change when the field strength is varied. Paramagnets or diamagnets change their magnetization, but the change is linear and, accordingly, cannot be recorded by am MPI installation, as only non-linear changes can be taken into account therein. This can be avoided by means of an apparatus 100 according to the approach described herein.

Figure 2:
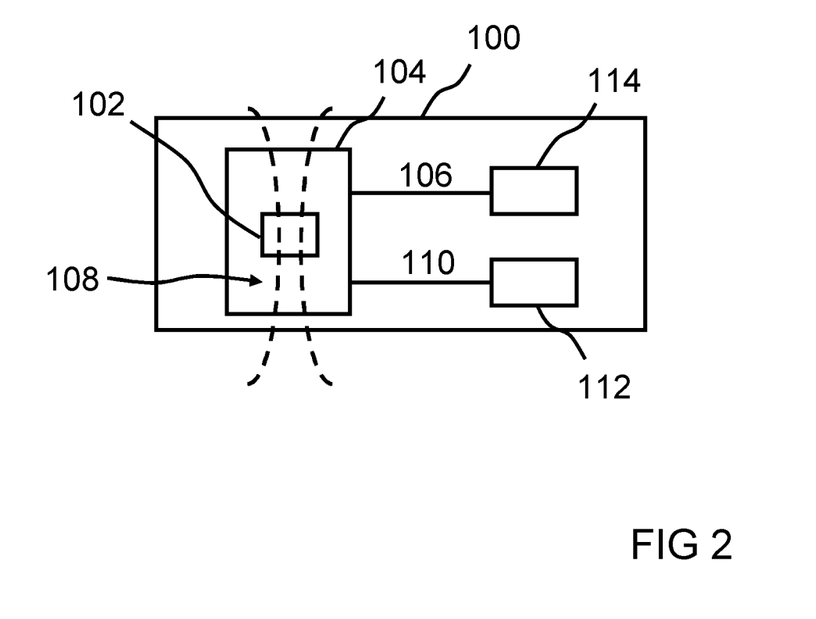

FIG. 2 shows a schematic illustration of an apparatus 100 for analyzing a sample volume 102 comprising magnetic particles, according to an embodiment. The apparatus 100 may correspond to the apparatus shown in FIG. 1 with the exception that, in the embodiment shown in FIG. 2, the sample volume 102 is or may be arranged inside the measuring coil 104, i.e. is surrounded by a plurality of windings of the measuring coil 104, for example.

The sample volume 102 may be introduced inside the measuring coil 104 for analyzing the sample volume 102.

Figure 3:
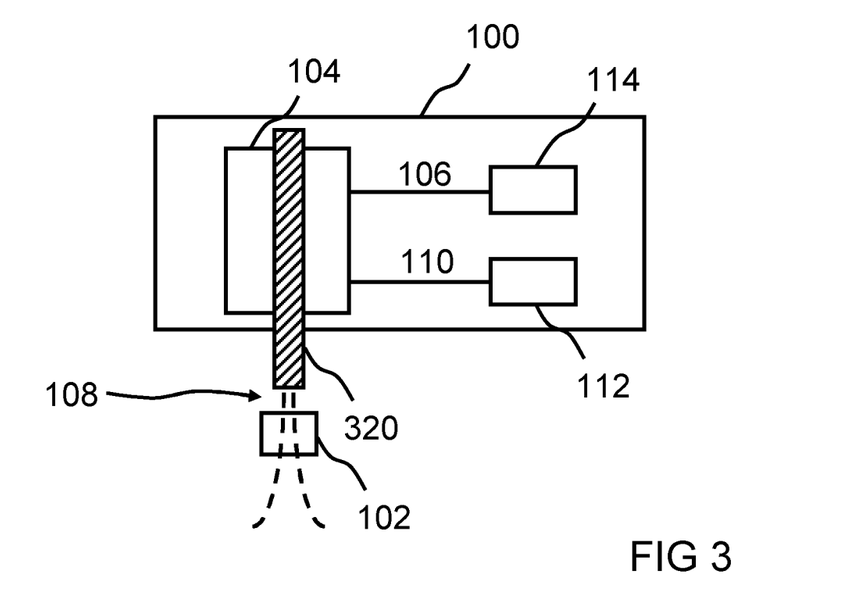

FIG. 3 shows a schematic illustration of an apparatus 100 for analyzing a sample volume 102 comprising magnetic particles, according to an embodiment. The apparatus 100 may correspond to the apparatus shown in FIG. 1 with the exception that a coil core 320 is guided through the measuring coil 104, and that the sample volume 102 is or may be arranged at one end of the coil core 320, according to the embodiment shown in FIG. 3.

Figure 4:
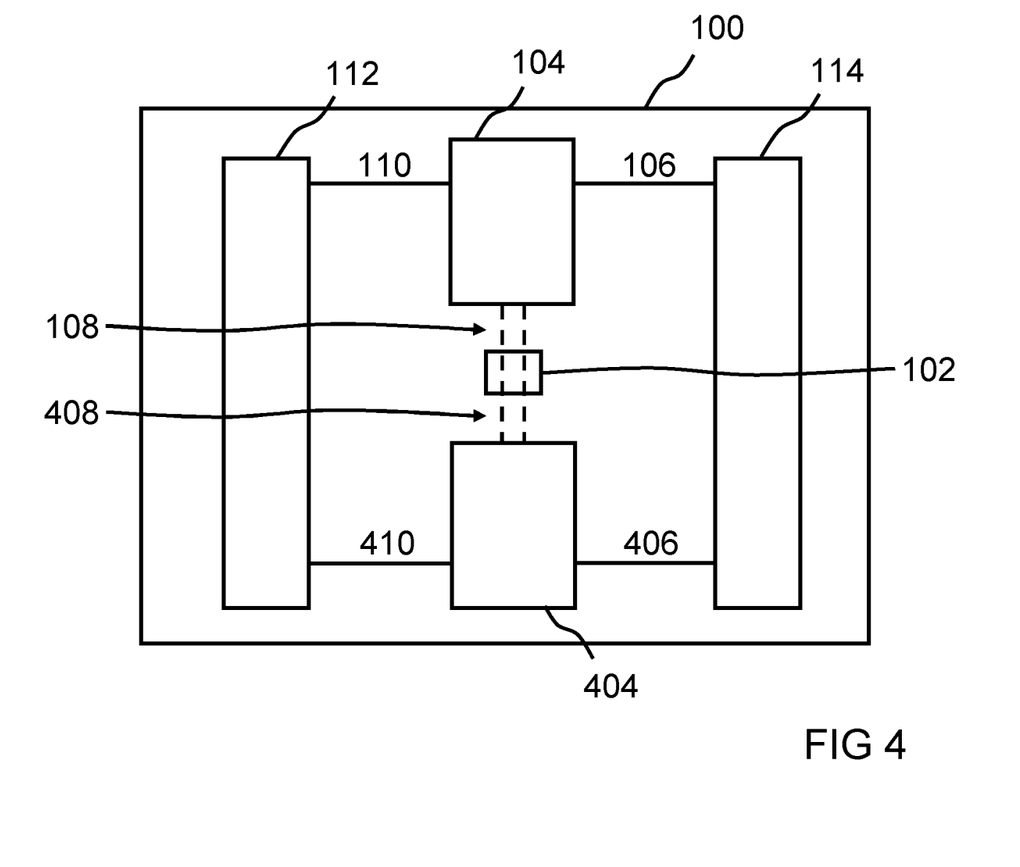

FIG. 4 shows a schematic illustration of an apparatus 100 for analyzing a sample volume 102 comprising magnetic particles, according to an embodiment. The apparatus 100 may correspond to the apparatus shown in FIG. 1 with the exception that the apparatus 100 comprises a further measuring coil 404, and that the sample volume 102 is or may be arranged between the two measuring coils 104, 404. For example, the measuring coils 104, 404 may comprise a common longitudinal axis extending through the sample volume 102.

When a further excitation signal 406 is applied to the further measuring coil 404, a further magnetic field 408 is generated by the further measuring coil 404. The further measuring coil 404 and the sample volume 102 are aligned with respect to each other so that the further magnetic field 408 acts on the sample volume 102, e.g. pervades it. The inductance of the further measuring coil 404 is dependent on the magnetic permeability of the sample volume 102. The magnetic permeability of the sample volume 102 can be gathered from the inductance of the further measuring coil 404. To this end, the apparatus 100 comprises a further measurement interface for sensing a further electric measurement signal 410 dependent on the inductance of the further measuring coil 404. The inductance of the further measuring coil 404 and hence the magnetic permeability of the sample volume 102 can be determined via the further measurement signal 410.

According to this embodiment, the evaluation means 112, which may again be realized as internal or external means with respect to the apparatus 100, is formed to sense and evaluate the two electric measurement signals 110, 410 for analyzing the sample volume 102. For evaluating the measurement signal's 110, 410, the evaluation means 112 may additionally receive and use information on the excitation signal's 106, 406 for evaluating the measurement signals 110.

The excitation means 114 is formed to generate the excitation signal's 106, 406 and provide the same to the measuring coils 104, 404. According to an embodiment, the excitation means 114 is formed to provide the excitation signals 106, 406 with different characteristics, for example different phases. Information on the characteristics of the excitation signal's 106, 406 may be provided to the evaluation means 112 by the excitation means 114 via an interface.

FIG. 5 shows a schematic illustration of an apparatus 100 for analyzing a sample volume 102 comprising magnetic particles, according to an embodiment. The apparatus 100 may correspond to the apparatus shown in FIG. 4 with the exception that the measuring coils 104, 404 are arranged next to each other, i.e. longitudinal axes of the measuring coils 104, 404 are parallel to each other, according to this embodiment. According to this embodiment, the further measuring coil 404 is used to analyze a further sample volume 502. As an alternative, the measuring coils 104, 404 may be used to analyze a common sample volume including the sample volumes 102, 502 shown.

The evaluation means 112 may be formed to evaluate the sample volumes 102, 502 separately or two generate a spatial distribution of magnetic particles within the common sample volume. For example, the evaluation means 112 may be formed to produce an image representation of the spatial distribution of the magnetic particles or a representation of the magnetic permeability within the common sample volume 102, 502.

For analyzing the sample volume is 102, 502, the evaluation means 112 may use information on characteristics of the excitation signal's 106, 406 and information on positions, for example relative positions, of the sample volumes 102, 502 or of the measuring coils 104, 404.

Additionally or alternatively, the evaluation means 112 may receive information on a characteristic of the additional magnetic field 530 and use the same for analyzing the sample volumes 102, 502. According to this embodiment, the additional magnetic field 530 is generated by means 532 for generating the additional magnetic field 530, for example by an arrangement of one or more magnets and one or more coils. The means 532 may also be part of the apparatus 100. The additional magnetic field 530 may, for example, be formed and employed as described with reference to FIG. 1.

Figure 6:
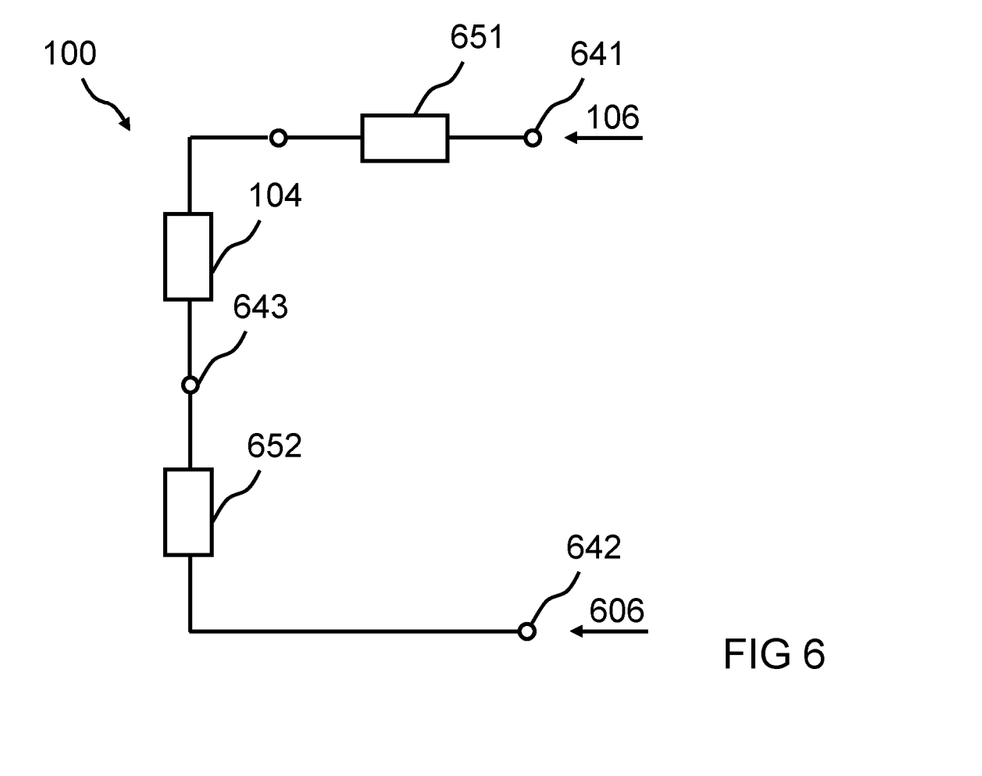

FIG. 6 shows a schematic illustration of an apparatus 100 for analyzing a sample volume 102 comprising magnetic particles, according to an embodiment. What is shown is a possible connection of the measuring coil 104 of the apparatus 100. Such connection may also be employed in the apparatuses 100 shown in the preceding figures.

The apparatus 100 comprises a first terminal 641, a second terminal 642 and a measurement interface 643.

A first contact of the measuring coil 104 is connected to the first terminal 641 wire a first element 651, for example a capacitor. A second contact of the measuring coil 104 is connected to the measurement interface 643 and to the second terminal 642 via a second element 652, for example a resistor.

And excitation signal 106, as described with reference to the preceding figures, may be fed in via the first terminal 641. To this end, the first terminal 641 can be connected to a suitable excitation circuit, such as described with reference to FIG. 1.

A balancing signal 606 may be fed in via the second terminal 642. To this end, the first terminal 641 may, for example, also be connected to the excitation circuit, which is formed to provide the balancing signal 606 in addition to the excitation signal 106.

According to an embodiment, a measurement signal, as already described, is applied to the measurement interface 643 during the analysis procedure of the apparatus 100. The measurement signal may, for example, be sensed and evaluated by evaluation means 112 so as to analyze the sample volume.

According to another embodiment, during the analysis procedure, the balancing signal 606 is fed into the second terminal 642 such that a predetermined steady reference signal is applied to the measurement interface 643. To this end, the balancing signal 606 may, for example, be regulated by regulation means using the signal applied to the measurement interface 643 so that the reference signal is applied to the measurement interface 643. The balancing signal resulting therefrom may then be evaluated by the evaluation means 112 as measurement signal in order to analyze the sample volume.

Figure 7:
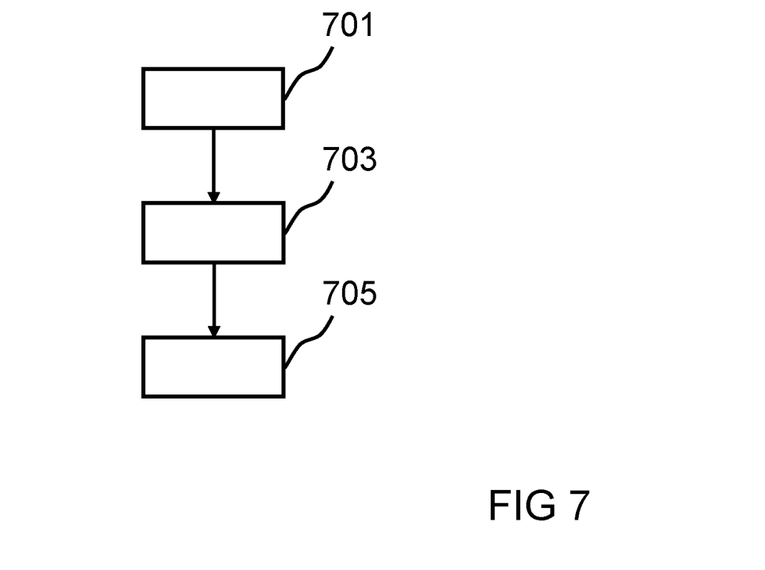
FIG. 7 shows a flowchart of a method for analyzing a sample volume, according to an embodiment.

FIG. 7 shows a flowchart of a method for analyzing a sample volume comprising magnetic particles, according to an embodiment. The method may, for example, be applied in connection with an apparatus as described with reference to the preceding figures.

In block 701, an electric excitation signal is applied to a measuring coil. Excited by the excitation signal, the measuring coil is formed to generate a magnetic field acting on the sample volume. In block 703, an electric measurement signal dependent on the inductance of the measuring coil is sensed. In block 705, magnetic permeability of the sample volume is analyzed on the basis of the measurement signal.

According to an embodiment, the measurement signal may be analyzed using a reference signal in block 705. The reference signal can be ascertained by executing the blocks 701, 703 of the method while the magnetic field of the measuring coil acts on a reference volume. The reference signal or a value corresponding to the reference signal may, for example, be stored in storage means after determination and read from the storage means.

According to an embodiment, for example, such a method for analyzing a sample volume comprising magnetic particles may be applied in connection with an apparatus as described with reference to FIG. 6.

In the block 701, the excitation signal is applied to the first terminal of the apparatus and the balancing signal is applied to the second terminal of the apparatus. In the block 703, the signal applied to the measurement interface is sensed as measurement signal.

The balancing signal to be applied in the blocks 701 may be ascertained and stored previously by executing the blocks 701, 703 of the method while the magnetic field of the measuring coil acts on a reference volume. Here, the balancing signal is adjusted so that a reference signal is applied to the measurement interface.

If the acts of the method are executed while the magnetic field of the measuring coil acts on the sample volume, the measurement signal is different from the reference signal in spite of the unchanged excitation signal and balancing signal, provided that the magnetic permeability of the sample volume is different from the reference volume. The magnetic permeability of the sample volume may thus be inferred from the difference between the reference signal and the measurement signal and in case the magnetic permeability of the reference volume is known.

According to a further embodiment, the excitation signal is applied to the first terminal of the apparatus and the balancing signal is applied to the second terminal of the apparatus in the block 701. Here, the balancing signal is adjusted so that a reference signal appears at the measurement interface. When analyzing different sample volumes, the balancing signal is adjusted each time so that the reference signal is applied to the measurement interface.

If the acts of the method are executed while the magnetic field of the measuring coil acts on the sample volume, the balancing signal is different from the balancing signal adjusted for a reference volume in spite of an unchanged excitation signal, provided that the magnetic permeability of the sample volume is different from the reference volume. The magnetic permeability of the sample volume may be inferred from the deviation of the balancing signal is adjusted for the reference volume and the sample volume, in case the magnetic permeability of the reference volume is known. The balancing signal adjusted for the reference volume or a value corresponding to this balancing signal may be stored in storage means and read out from the storage means in the block 705 of analyzing.

According to another embodiment, the method may be applied using two or more measuring coils so as to analyze two or more sample volumes.

To this end, in the block 701, an electric excitation signal is provided to a measuring coil and at least one further electric excitation signal is provided to at least one further measuring coil. In the block 703, measurement signal is dependent on the inductance is of the measuring coils are sensed and evaluated in the block 705, in order to analyze the sample volume or the sample volumes.

In the block 705, information on characteristics of the excitation signal is and additionally or alternatively characteristics of one or more additional magnetic field acting on the sample volume or volumes may also be used to evaluate the measurement signals. Here, in the block 705, a spatial distribution of kinetic particles or values of the magnetic permeability within the sample volume or volumes may be ascertained.

Figure 8:
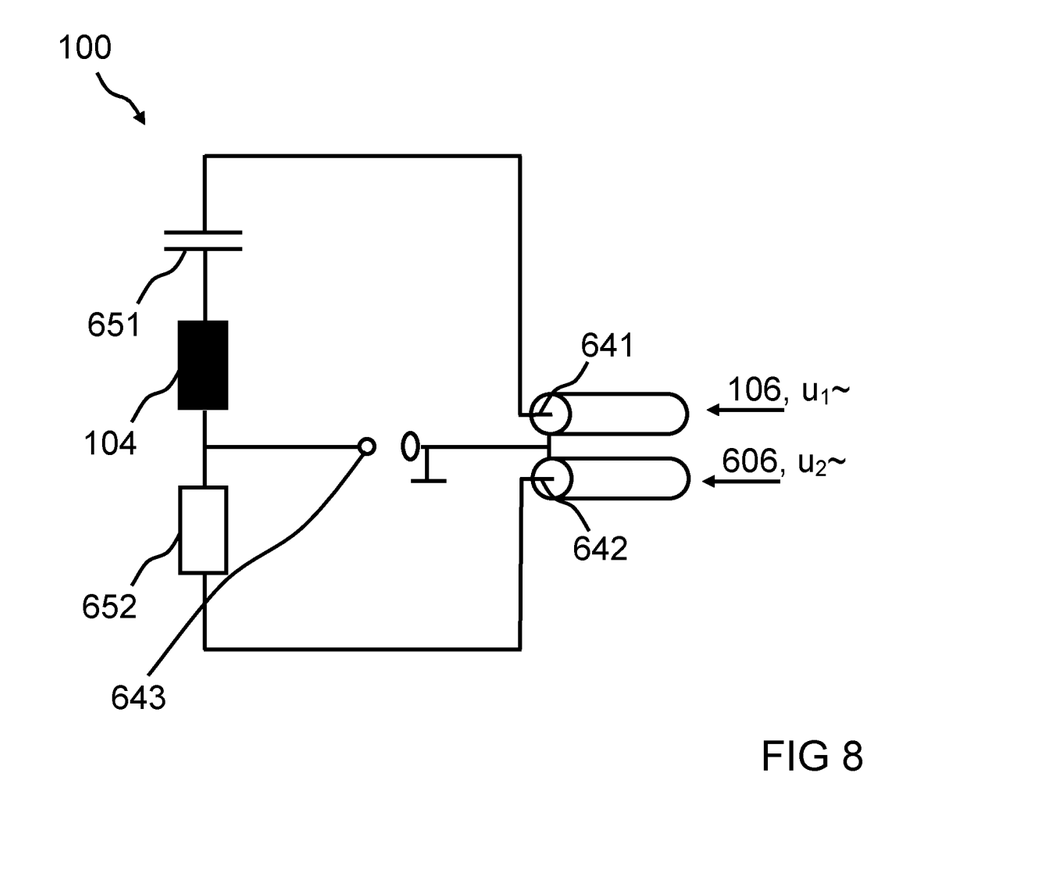
FIGS. 8 to 9 show schematic illustrations of an apparatus for analyzing a sample volume, according to embodiments.

FIG. 8 shows a schematic illustration of an apparatus 100 for analyzing a sample volume comprising magnetic particles, according to an embodiment. What is shown is a possible connection of the measuring coil 104 of the apparatus 100. Such connection may also be employed in the apparatuses 100 shown in the preceding figures.

The apparatus 100 comprises a first terminal 641, a second terminal 642 and a measurement interface 643.

A first contact of the measuring coil (L) 104 is connected to the first terminal 641 via a first element 651, here a capacitor (C). A second contact of the measuring coil 104 is connected to the measurement interface 643 via a line and to the second terminal 642 via a second element 652, here a resistor (R).

An excitation signal 106, here in form of a first alternating voltage U1~, may be supplied via the first terminal 641 via a first coaxial line, for example. A balancing signal 606, here in form of a second alternating voltage U2~, may be supplied via the second terminal 642 via a second coaxial line, for example.

Depending on the embodiment, the measurement signal already described or the reference signal already described may be tapped between the measurement interface 643 and a ground connection 845 of the apparatus 100.

Figure 9:
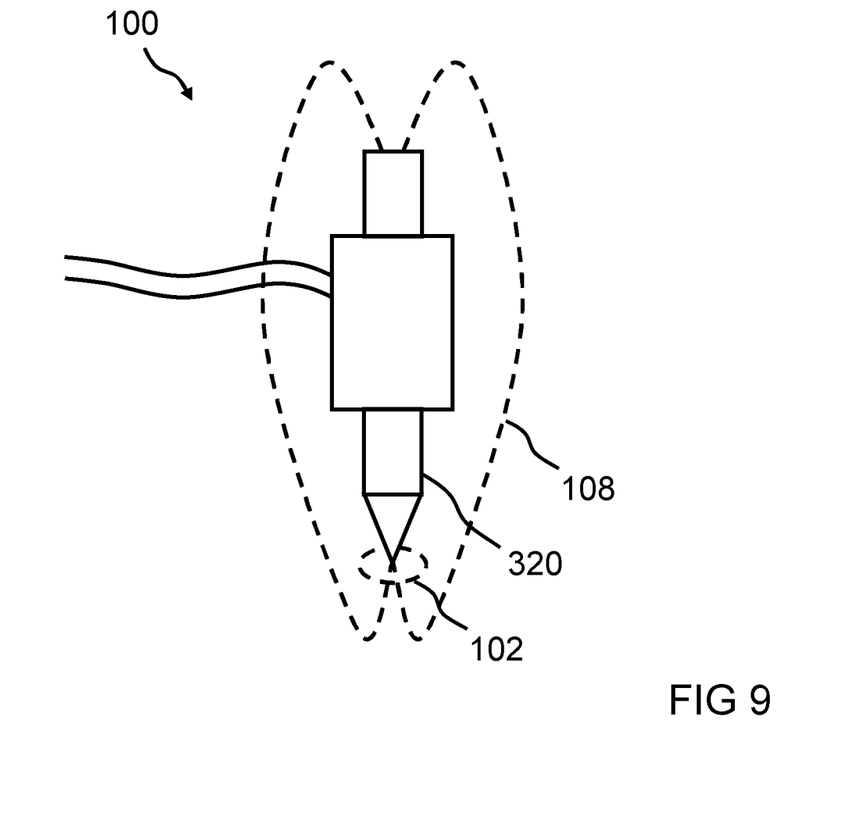

FIG. 9 shows a schematic illustration of an apparatus 100 for analyzing a sample volume comprising magnetic particles, according to an embodiment. The apparatus 100 comprises a measuring coil with a coil core 320, as described with reference to FIG. 3, for example. The coil core is formed as a cylindrical rod having a flat end at one end and a tip at the other end. The tip is guided into a sample volume 102 or directed to the sample volume 102. Through the tip of the coil core 320, the magnetic field lines of the magnetic field 108 are concentrated on the sample volume 102. The apparatus 100 comprises two electric lines, for example, as an interface for energizing or for supplying or reading out signals.

Various embodiments shall be described in the following with reference to the preceding figures.

Measurement of the magnetic permeability forms the basis of the embodiments.

The magnetic permeability as the property of conducting a magnetic field in matter is accessible directly via the inductance of the coil 104 generating the alternating field. This allows for advantageous construction of such a measuring apparatus 100. In the simplest case, it comprises a single coil 104, which generates a magnetic field 108 of certain strength in a measurement volume 102 when applying an alternating voltage 106. The inductance of the coil 104 directly depends on the magnetic permeability and can be determined by way of simple current or voltage measurement, for example via the measurement signal 110. By way of a suitable electric connection, such as a bridge circuit in combination with voltage metering, it is easily possible to adjust the measured voltage signal 110 so that the measured voltage 110 only corresponds to the change in the voltage 110 resulting from introduction of a sample into the sample volume 102 and hence from a change in the magnetic permeability. Thus, the dynamic range of a voltage meter of the voltage 110 may be used for the relevant information.

According to an embodiment, such a measuring bridge comprises a coil 104 capable of generating a field in the sample volume 102 and an electric resistor 652. The voltage applied via the excitation signal 106 at the measuring coil 104 is selected so that the selected magnetic field 108 is generated. The voltage applied via the balancing signal 606 at the bridge resistor 652 is chosen correspondingly so that without a sample no voltage 110 drops at the voltage meter in the simplest case. When a sample is introduced into the volume 102 of the measuring coil 104, the magnetic permeability of the sample can be determined from the voltage curve 110, depending on the applied magnetic field strength of the field 108. The presence and properties, such as the amount of substance, of the magnetic material in the sample volume 102 may be inferred therefrom.

According to an embodiment, the voltage U1~ 106 is selected so that a suitable alternating magnetic field 108 is generated in the coil 104. As a matter of principle, the capacitor 651 shown in FIG. 8 is not necessary, but a good option for reducing the reactance, so that a high current can be generated at low voltage. Specifically, a sinusoidal voltage at a frequency, e.g. 20 kHz, is suited as excitation signal 106. The field 108 generated thereby ideally is greater than 5 mT at the tip, and may reach several 100 mT. With respect to its temporal course, the voltage U2~ 606 is selected so that a voltage of 0V always is generated as reference signal at the output 643, i.e. the voltage between ground and the connection of coil 104 and resistor 652, in the case of an empty measuring coil 104, i.e. empty sample volume 102. In the simplest case, the balancing voltage 606 also is a sinusoidal voltage at a certain level and a certain phase with respect to the voltage U1~ 106. When a magnetizable sample is introduced into the coil 104 or brought in proximity to the coil 104, voltage curve dependent on the magnetic permeability of the sample in the sample volume 102 is obtained at the output 643.

A measuring bridge as shown in FIG. 8, for example, has two fundamental modes of operation, bridge balancing and measurement of bridge voltage.

In bridge balancing, the time-dependent voltage at the resistor is adjusted so that the bridge voltage at the measurement interface 643 always becomes zero. The actual measurement signal 110 is the difference between the voltage at the resistor 652 with and without a sample in the sample volume 102.

When measuring the bridge voltage, the voltage at the resistor 652 is adjusted so that the bridge voltage at the measurement interface 643 becomes zero when the measuring coil 104 is empty, i.e. when the sample volume 102 is empty. Now, the measured bridge voltage is the actual measurement signal 110.

It is also possible to use a combination of these two modes and thus obtain a sum of the dynamic range of the voltage meter and the voltage at the resistor 652 as the dynamic range.

This measurement arrangement may also be realized in other embodiments. Instead of voltage metering, also current measurement may be conducted.

What is advantageous with large measurement volumes 102, in particular, is resonant matching of the measurement coil 104 with the frequency of the alternating field 108, so that operation may be at lower voltage. According to an embodiment, the coil 104 is connected in series with a suitably selected capacitor 651. Also, the bridge resistor 652 shown in FIG. 8 may be replaced by a more complex arrangement of coils, capacitors and resistors. In some cases, it is advantageous for suppressing interference from the surrounding space to select a coil of opposite field direction and similar to the measuring coil 104. This arrangement acts like a gradiometer, wherein a voltage signal equally generated in both coils is canceled out. More complex arrangements of electric components may also be connected in parallel or in series to the measuring coil 104 so as to adapt the properties, such as resonances.

A particular implementation of such a measurement system 100 is a coil 104 enclosing a measurement volume 102 and generating a homogeneous alternating field 108 there. Another particular arrangement is a measuring coil 104 capable of generating, in front of a surface, a magnetic field 108, which is homogeneous or decreasing in strength in linear manner with respect to the distance from the surface.

It is conceivable that this measuring apparatus 100 is particularly suited for measuring at the excitation frequency, as resonant matching makes it particularly sensitive at exactly this frequency. However, this is not a disadvantage because this makes for valuable information and because nonlinearities of the magnetic permeability, above all, lead to a series of higher harmonics for which then wideband measurement is necessary. Due to that, resonant matching with another frequency makes only limited sense. Nevertheless, it is not necessary to resonantly match the measuring coil 104 with the excitation frequency. As a matter of principle, the matching may instead also be made with another frequency, and a series of known approaches for multi-resonant matching of coils are available.

Localization of the particles within the sample volume 102 is done by one or a combination of the following mechanisms.

If the coil 104 is sensitive only locally, the particles can be determined locally hereby. It is to be noted here that this design may easily be miniaturized and thus integrated into a catheter, for example. Thus, local measurement of magnetized particles can be done in blood vessels, for example.

One particular extension is the possibility of using one or more magnetically conductive cores 320 in this measuring arrangement 100 for conducting the field 108 two another location. For example, it is possible to set a needle of ferromagnetic material into the coil 104, as shown in FIG. 9. The coil 104 generates a moderate magnetic flux which can be kept below saturation in the core 320, but a high flux at the tip of the needle. Magnetizable particles in the region 102 of the tip of the needle generate a particularly high response signal, because the magnetization is highest here. Thus, a microscope can be realized.

For example, the arrangement shown in FIG. 9 generates a high local field in the region indicated, which may serve as sample volume 102. A further measuring arrangement, which may be employed in addition, is not depicted here.

Localization of particles by means of an apparatus 100 as described with reference to the figures may be done by way of an array setup of individual measuring coils 104, 404. Here, in the simplest case, e.g. for two-dimensional measurement one an object's surface, the array setup can be done such that the individual elements with the individual measuring coils 104, 404 measure bordered measurement volumes 102, 502 of their own, and an image is calculated therefrom.

According to an embodiment, the individual elements with the individual measuring coils 104, 404 may be arranged such that the individual measurement takes place in overlapping volumes 104, 404. Here, by way of a suitable field profile of the fields 108, 408 of the individual coils 104, 404, such as homogeneous excitation fields or excitation field gradients in combination with an individual or equal frequency, amplitude and phase of the excitation voltage, a locally different, time-dependent magnetic field differing in amplitude and/or phase may be generated. By suitable combination of excitation patterns, an image may be calculated therefrom. A simple example for illustration consists in e.g. to opposite coils 104, 404, such as shown in FIG. 4, whose magnetic fields 108, 408 is selected through construction of the coils 104, 404 in the measurement volume 102 therebetween so that, if the two coils 104, 404 are driven with different phases of the alternating voltage, the amplitude of the overall magnetic field is approximately equal, but a different phase is obtained, depending on which coil 104, 404 is closer. The magnetic permeability (generally a complex value) of a spot sample shows the location between the coils 104, 404 via its phase (one-dimensional here).

Such setups may be optimized individually depending on the measuring object, such as the linear stringing of conductor loops for cylindrical objects for one-dimensional measurement. Correspondingly, three-dimensional coding of a location can be done with several such opposite coils 140, 404 in a three-dimensional arrangement.

It is also possible to change, and thereby locally encode, the magnetic permeability by way of additional magnetic fields 530, such as externally generated magnetic field gradients, by way of Anti-Helmholtz coils in the simplest case. Such an arrangement is shown in FIG. 5, for example. In this case, the nonlinear magnetic permeability, which is very similar to the magnetization, can be measured and used for image reconstruction.

The magnetic permeability in strong magnetic fields, such as that of MRI, is a measurable quantity and may also be employed for particle detection and characterization here.

In a simple example, localization and characterization of the particles by way of a locally sensitive coil, such as a catheter with integrated measuring coil 104, may locally measure the presence of particles. By way of example, the presence of a paramagnetic substance, such as Dysprosium (III) oxide, may thus be determined. The other techniques presented may also be employed, however.

According to an embodiment, the apparatus 100 shown is implemented as a spectrometer for detecting magnetic particles which may be in a corresponding sample volume 102. What is special here is that only a single coil 104 is needed for generating an excitation and detection field 108. Due to the particular electric connection of the coil 104 it is possible to obtain the signal of the magnetic particles in a background-free manner without particular arrangements concerning the construction of the coil 104.

It is to be noted here that this arrangement is particularly suited for picking up signals at the excitation frequency of the coil 104. Thus, it is possible to measure also particles with linear magnetization depending on the field strength, such as usually exhibited by diamagnets and paramagnets.

Such a spectrometer may be operated both on its own as a spectrometer for magnetic particles and as part of an imaging setup. Static magnetic fields 530 may also be realized as offset for the measurement in the setup, just as co-action with externally generated, static, magnetic offset fields 530.

The magnetic permeability of magnetic nanoparticles gives important information about the particles themselves, but also about their environment. Thus, it is possible to determine concentrations of particles, but also properties of the particles, such as size or temperature. The environment also has an influence, for example the viscosity of the surrounding medium may have an effect on the signal and thus be measured.

Given suitable choice of the particles, such as particles having a non-linear magnetization curve, i.e. the magnetization and hence the magnetic permeability of the particles increases in non-linear manner with an applied magnetic field, and a locally variable magnetic field 530, local association of the signal can be performed and thus an image can be generated.

In particular, localization of magnetizable substances is possible, such as ferrite particles or paramagnetic substances.

Miniaturization of a measuring probe for such substances may be done here, e.g. for a catheter.

Detection of such substances is also possible in strong magnetic fields, such as are present e.g. in MRI. In particular, localization of such substances in strong magnetic fields 530 also can be realized.

According to an embodiment, a magnetizable sample 102 is introduced into the coil 104, and the voltage curve of the measurement interface 643 serving as an output is evaluated. The voltage curve at the measurement interface 643 here is dependent on the magnetic permeability of the sample 102.

Likewise, the current in the coil 104 may also be measured. The current is also dependent on the magnetic permeability of the sample 102.

Such a measurement may be used for the localization of particles.

This may be done also in connection with measuring arrays or measuring fields by way of miniaturization of the measuring arrangement 100.

It is possible to achieve localization through the use of a needle-shaped magnetically conductive core 320. Here, a large magnetic field 108, in which the particles may be detected, is generated locally at the tip of the needle of the core 320.

The localization may be generated by spatially variable amplitudes and/or phase change of the generated measuring magnetic field 108.

Locally variable, static or quasi-static, additional magnetic fields 530 may be used.

The functionality is similar to Magnetic Particle Imaging (MPI) with the exception that a physically different parameter of the sample is measured here. The magnetization can be calculated from the permeability. It is easier and metrologically advantageous to measure the magnetic permeability. Thus, paramagnetic and diamagnetic substances may also be measured. Furthermore, it is possible to conduct the measurement also in strong magnetic fields 530, such as in magnetic resonance tomographs.

The MPI measures the change in magnetization M, whereas the method presented herein measures the magnetic permeability.

Figure 10:
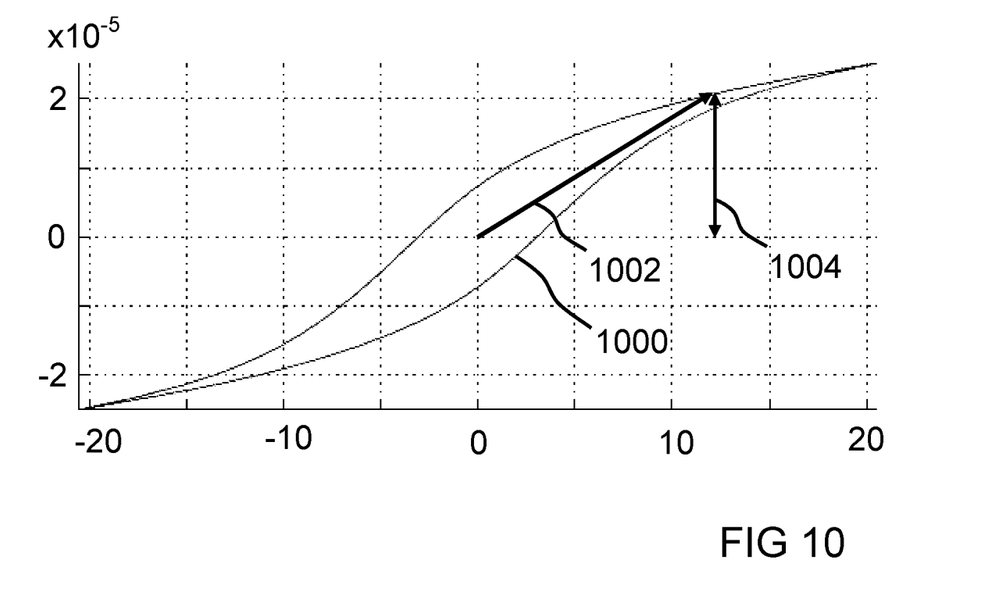
FIG. 10 shows an illustration of magnetization.

FIG. 10 shows a magnetization curve of superparamagnetic nanoparticles as a suspension or slurry. The magnetic permeability is determined as follows:

Magnetic permeability=((magnetization)/(field strength)+1)

The field strength is plotted in mT on the X-axis, and the magnetization is plotted in Am$^2$ on the Y-axis. What is shown is the magnetization curve 1000 of the particles. The arrow 1002 symbolizes something like magnetic susceptibility (M/H), and the Y-axis intercept 1004 approximately symbolizes the magnetization M (for about 12 mT excitation field here).

The approach described may be realized in various embodiments. Miniaturization of the setup 100 for local determination is possible. Also, the array setup 100 can be realized, like linearly strong coils 104, 404 arranged around the sample 102, with suitable choice of amplitude and phase among the individual coils 104, 404. Furthermore, static or quasi-static additional magnetic fields 530 with magnetic field gradients within the measurement volume 102 of the coil 104 or coils 104, 404 may be employed.

With reference to the embodiment shown in FIG. 8, a number of capacitors, resistors and coils may be connected in parallel and/or in series with respect to the coil 104, just like to the resistor 652. Hereby, manual coarse adjustment may, for example, be realized in a simple manner if one or more of these elements are adjustable.

The resistor 652 may be realized by way of a coil. This can be advantageous if little phase shift of the voltages U1~, U2~ 106, 606 is desired. This coil may be connected such that, similar to a gradiometer, externally induced interferences generate a voltage swing of opposite sign and cancel each other out in the end. This may also be utilized to get by with a lower voltage U2~ 606.

The coil 104 may be formed so as to be able to generate a homogeneous field 108 in its interior. This is advantageous for measuring samples 102 in test tubes, for example.

The coil 104 may be formed so as to generate a homogeneous field 108 in a certain region in front of a planar area, also a corresponding non-homogeneous field 108. Hereby, extensive objects 102 can be examined locally by means of a small sensor 100.

A number of such measuring coils 104 may simultaneously perform local measurements of adjacent measurement volumes 102, 502 by way of suitable arrangement, e.g. as an array. Ideally, the individual coils 104, 404 are geometrically, inductively or competitively decoupled here.

In an arrangement of coils 104, 404, spatial resolution of the picked-up signal may also be achieved through suitable selection of amplitudes, phases and frequencies of the individual elements and suitable reconstruction of the measurement signal.

This setup 100 may also work together with externally generated magnetic fields 530, such as static homogeneous fields or time-variant homogeneous fields.

Likewise, this setup 100 may also work together with spatially and/or temporarily varying in homogeneous fields 530. By way of suitable reconstruction, the measured information may also be associated spatially.

According to an embodiment, this setup 100 also serves to detecting magnetizable particles, including ones having linear and non-linear magnetizability when a magnetic field is applied.

According to an embodiment, the setup 100 shown in FIG. 8, for example, has two fundamental modes of operation, in one of which the voltage U2~ 606 is selected such that the empty measuring coil 104 does not provide an output signal, wherein the measurement signal 110 here is the voltage at the output 643 in case of a sample 102 in the measuring field 108. The other mode of operation consists in always selecting the voltage U2~ 606 such that no voltage is generated at the output 643, wherein the measurement signal 110 is the difference of the voltage U2~ 606 in case of the sample 102 in the measuring field 108 and the voltage U2~ 606 without any sample 102 in the measuring field 108. It is also possible to choose any combination of both methods. Thus, the maximum measurement voltage may, for example, be limited. The resulting dynamic range here is the sum of the dynamic ranges of the voltage U2~ 606 and the voltage metering.

A particular extension is the possibility of using magnetically conductive cores 320 in this measurement setup 100 for conducting the field 108 to another location. Thus, for example, it is possible to install a needle of ferromagnetic material into the coil 104. The coil 104 generates a moderate magnetic flux in the core 320, but a high one at the tip of the needle. Magnetizable particles in the region of the tip of the needle generate a particularly high response signal, because magnetization is highest there. Hence, a microscope may be realized.

The embodiments described are only exemplary and may be combined with each other.

What is claimed is:

1. A method of analyzing a sample volume comprising magnetic particles having a non-linear magnetization curve by using a measuring bridge comprising a single coil and an electric resistor, wherein the measuring bridge does not comprise a reference coil, the method comprising:
applying an electric excitation signal to the single coil formed as a measuring coil to generate a magnetic field acting on the sample volume using the measuring coil, wherein a first contact of the measuring coil is connected to a first terminal for applying the electric excitation signal via a first element, a second contact of the measuring coil is connected to a second terminal for applying an electric balancing signal via a second element formed as the electric resistor, and the second contact of the measuring coil is connected to a measurement interface, and wherein, in the applying, the excitation signal is applied to the first terminal and the balancing signal is applied to the second terminal;
sensing an electric measurement signal dependent on the inductance of the measuring coil,
wherein, in the sensing, the measurement signal is sensed at the measurement interface, with the balancing signal representing a signal with which a reference voltage is present at the measurement interface if the magnetic field generated by the measuring coil acts on a reference volume, or wherein, in the sensing, the balancing signal is sensed as the measurement signal, with the balancing signal being formed to set a certain reference voltage at the measurement interface independently of whether the magnetic field generated by the measurement coil acts on the sample volume or a reference volume; and analyzing nonlinear magnetic permeability of the sample volume using the measurement signal.

2. The method of claim 1, further comprising comparing the measurement signal to a reference signal so as to determine the magnetic permeability of the sample volume, with the reference signal representing a further electric measurement signal dependent on the inductance of the measuring coil while the measuring coil generates a magnetic field acting on a reference volume.

3. The method of claim 1, further comprising:

applying a further electric excitation signal to a further measuring coil so as to generate a further magnetic field acting on a further sample volume using the further measuring coil, and sensing a further electric measurement signal dependent on the inductance of the further measuring coil, with the further measurement signal allowing for analysis of the magnetic permeability of the further sample volume due to the dependence of the inductance of the further measuring coil on the magnetic permeability of the further sample volume.

4. The method of claim 3, further comprising determining a distribution of the magnetic particles in the sample volume and in the further sample volume using the measurement signal, the further measurement signal and information on a position of the sample volume, a position of the further sample volume, information on a characteristic of the excitation signal and information on a characteristic of the further excitation signal.

5. The method of claim 1, further comprising exposing the sample volume to an inhomogeneous additional magnetic field, and wherein, in the analyzing, a distribution of the magnetic particles in the sample volume is determined using the measurement signal and information on a spatial course of the additional magnetic field within the sample volume.

6. The method of claim 5, wherein the applying, the sensing and the exposing are executed repeatedly, wherein the spatial course of the additional magnetic field is changed in the multiple acts of exposing the sample volume, and wherein, in the analyzing, the distribution of the magnetic particles is determined using the measurement signal as sensed in the multiple acts of sensing and information on a change of the spatial course of the additional magnetic field during the multiple acts of exposing.

7. An apparatus for analyzing a sample volume comprising magnetic particles having a non-linear magnetization curve, the apparatus comprising:

a measuring bridge comprising a single coil and an electric resistor, wherein the measuring bridge does not comprise a reference coil, wherein the single coil is formed as a measuring coil formed to generate a magnetic field acting on the sample volume in response to applying an electric excitation signal to the measuring coil, wherein a first contact of the measuring coil is connected to a first terminal for applying the electric excitation signal via a first element, a second contact of the measuring coil is connected to a second terminal for applying an electric balancing signal via a second element formed as the electric resistor, and the second contact of the measuring coil is connected to a measurement interface, and wherein the excitation signal is applicable to the first terminal and the balancing signal is applicable to the second terminal: and the measurement interface is for sensing a measurement signal dependent on the inductance of the measuring coil, wherein the measurement signal is sensable at the measurement interface, with the balancing signal representing a signal with which a reference voltage is present at the measurement interface if the magnetic field generated by the measuring coil acts on a reference volume, or wherein the balancing signal is sensable as the measurement signal, with the balancing signal being formed to set a certain reference voltage at the measurement interface independently of whether the magnetic field generated by the measuring coil acts on the sample volume or a reference volume, and with the measurement signal allowing for analysis of the nonlinear magnetic permeability of the sample volume due to the dependence of the inductance of the measuring coil on the magnetic permeability of the sample volume.

8. The apparatus of claim 7, wherein the sample volume is arranged inside the measuring coil.

9. The apparatus of claim 7, further comprising a coil core guided through the measuring coil, wherein one end of the coil core is formed as a tip for exposing the sample volume.

10. The apparatus of claim 7, wherein the first element is a capacitor or an electric line, and the second element is a resistor, a coil or an electric line.

11. The apparatus of claim 7, further comprising a further measurement coil formed to generate a further magnetic field acting on a further sample volume in response to applying a further electric excitation signal to the further measuring coil, comprising a further measurement interface for sensing a further electric measurement signal dependent on the inductance of the further measuring coil, with the further measurement signal allowing for analysis of the magnetic permeability of the further sample volume due to the dependence of the inductance of the further measuring coil on the magnetic permeability of the further sample volume.

12. The apparatus of claim 11, wherein the sample volume and the further sample volume overlap at least partially.

* * * * *